United States Patent [19]
Djuric et al.

[11] Patent Number: 5,508,309
[45] Date of Patent: Apr. 16, 1996

[54] LTB4 SYNTHESIS INHIBITORS

[75] Inventors: Stevan W. Djuric, Glenview; Richard A. Haack; Julie M. Miyashiro, both of Chicago, all of Ill.

[73] Assignee: G. D. Searle & Co., Chicago, Ill.

[21] Appl. No.: 271,381

[22] Filed: Jul. 1, 1994

Related U.S. Application Data

[63] Continuation of Ser. No. 707,522, May 30, 1991, Pat. No. 5,356,919.

[51] Int. Cl.$^6$ .................... A61K 31/19; A61K 31/235; A61K 31/215
[52] U.S. Cl. .................... 514/568; 514/533; 514/544; 514/545; 514/570; 514/571; 562/459
[58] Field of Search .................... 562/459; 514/533, 514/544, 545, 568, 570, 571

[56] References Cited

U.S. PATENT DOCUMENTS

| | | | |
|---|---|---|---|
| 3,255,241 | 6/1966 | Schultz et al. | 260/516 |
| 3,912,656 | 10/1975 | Andrews et al. | 252/431 |
| 3,919,250 | 11/1975 | Pauling et al. | 260/340 |
| 4,015,010 | 3/1977 | Houlihan et al. | 424/308 |
| 4,381,360 | 4/1983 | Leistner et al. | 524/178 |
| 4,469,885 | 9/1984 | Mueller et al. | 562/459 |

FOREIGN PATENT DOCUMENTS

| | | |
|---|---|---|
| 142145 | 5/1985 | European Pat. Off. |
| 282898 | 9/1988 | European Pat. Off. |
| 1457025 | 12/1976 | United Kingdom . |

OTHER PUBLICATIONS

Fackler, *Progress Inorg. Chem.*, "Metal β-Ketoenolate Complexes" pp. 361–425 (1966).
Singh, et al., *Progress in Medicinal Chem.*, vol. 17, Elseveer, Chap. 4–*Medicinal Chem. of Tetrazoles*, pp. 151–183 (1980).
Thornber, *Chem. Society Reviews*, vol. 8, pp. 563–580 (1979).

*Primary Examiner*—Bernard Dentz
*Attorney, Agent, or Firm*—Scott B. Feder; Roger A. Williams

[57] ABSTRACT

This invention relates to a compound of the formula:

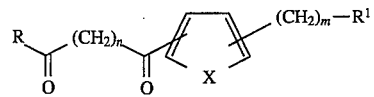

or a pharmaceutically acceptable salt thereof
  wherein X is oxygen, sulfur, —CH=CH—, or —CH=N—;
  wherein $R^1$ is —$CO_2R^2$ or tetrazole;
  wherein $R^2$ is hydrogen, alkyl of 1 to 6 carbons or a pharmaceutically acceptable cation;
  wherein R is an alkyl of from 1 to 20 carbons, —$(CH_2)_pCF_3$ or —$(CH_2)_qR^3$ wherein $R^3$ is alkoxy, phenoxy or alkoxy substituted phenoxy wherein the alkoxy group has from 1 to 8 carbons;
  wherein p and q are integers from 0 to 20;
  wherein n is 0 or 1; and
  wherein m is 0, 1, 2, or 3.

12 Claims, No Drawings

1

LTB4 SYNTHESIS INHIBITORS

This is a CONTINUATION of prior application Ser. No. 07/707,522 filed on May 30, 1991 now U.S. Pat. No. 5,356,919.

BACKGROUND OF THE INVENTION

The present invention relates to pharmaceutical agents (compounds) which act as leukotriene $B_4$ ($LTB_4$) synthesis inhibitors in mammals. The compounds inhibit $LTB_4$ synthesis by inhibiting phospholipase $A_2$ ($PLA_2$) activity. $PLA_2$ is an important enzyme in the biosynthesis of leukotrienes as $PLA_2$ acts to release arachidonic acid from phospholipids. Once released, arachidonic acid is rapidly metabolized by a variety of enzymes of the arachidonic acid cascade to produce prostaglandins, leukotrienes and related compounds. The use of the compounds herein to inhibit $PLA_2$ activity thus inhibits the release of arachidonic acid from phospholipids. The inhibition of release of arachidonic acid similarly diminishes subsequent products in the arachidonic acid cascade, such as prostaglandins, leukotrienes, and related compounds, including $LTB_4$.

$LTB_4$ (Formula I) is an arachidonic acid metabolite which is produced by the 5-lipoxygenase pathway. Pharmacologically, $LTB_4$ is an important mediator of

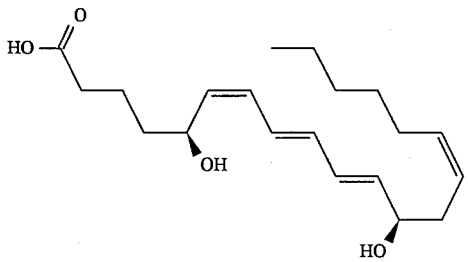

inflammation. $LTB_4$ is known to induce chemotaxis, chemokinesis, aggregation, and degranulation of leukocytes in vitro, and to induce accumulation of polymorphonuclear leukocytes, and increase vascular permeability and edema formation in vivo. Particularly high levels of $LTB_4$ are detected in lesions in inflammatory diseases such as rheumatoid or spondylarthritis, gout, psoriasis, ulcerative colitis, Crohn's disease, multiple sclerosis and some respiratory diseases. Since the compounds herein inhibit $PLA_2$ and thereby $LTB_4$ synthesis, the compounds of the present invention are useful in treating inflammatory conditions in mammals such as psoriasis, Crohn's disease, ulcerative colitis, multiple sclerosis and the like.

Accordingly, it is an object of this invention to produce compounds for use as pharmaceutical agents which will exhibit $LTB_4$ inhibitory activity in mammals.

The pharmacology of the biologically active leukotrienes is generally discussed in J. Clin. Invest. 73, 889–897 (1984).

SUMMARY OF THE INVENTION

This invention relates to a compound of the formula:

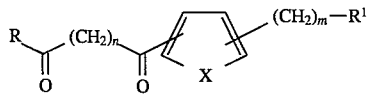

or a pharmaceutically acceptable salt thereof wherein X is oxygen, sulfur, —CH=CH—, or —CH=N—;

wherein $R^1$ is —$CO_2R^2$ or tetrazole;

wherein $R^2$ is hydrogen, alkyl of 1 to 6 carbons or a pharmaceutically acceptable cation;

wherein R is an alkyl of from 1 to 20 carbons, —$(CH_2)_pCF_3$ or —$(CH_2)_qR^3$ wherein $R^3$ is alkoxy, phenoxy or alkoxy substituted phenoxy wherein the alkoxy group has from 1 to 8 carbons;

wherein p and q are integers from 0 to 20;

wherein n is 0 or 1; and wherein m is 0, 1, 2, or 3.

This invention, more specifically, relates to a compound of the formula:

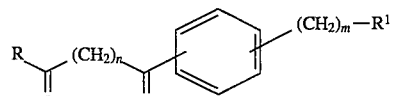

or a pharmaceutically acceptable salt thereof wherein X is oxygen, sulfur, —CH=CH—, or —CH=N—;

wherein $R^1$ is —$CO_2R^2$ or tetrazole;

wherein $R^2$ is hydrogen, alkyl of 1 to 6 carbons or a pharmaceutically acceptable cation;

wherein R is an alkyl of from 1 to 20 carbons, —$(CH_2)_pCF_3$ or —$(CH_2)_qR^3$ wherein $R^3$ is alkoxy, phenoxy or alkoxy substituted phenoxy wherein the alkoxy group has from 1 to 8 carbons;

wherein p and q are integers from 0 to 20;

wherein n is 0 or 1; and wherein m is 0, 1, 2, or 3.

This invention also relates to a compound of the formula:

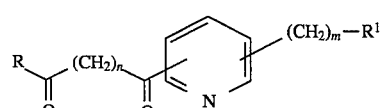

or a pharmaceutically acceptable salt thereof wherein X is oxygen, sulfur, —CH=CH—, or —CH=N—;

wherein $R^1$ is —$CO_2R^2$ or tetrazole;

wherein $R^2$ is hydrogen, alkyl of 1 to 6 carbons or a pharmaceutically acceptable cation;

wherein R is an alkyl of from 1 to 20 carbons, —$(CH_2)_pCF_3$ or —$(CH_2)_qR^3$ wherein $R^3$ is alkoxy, phenoxy or alkoxy substituted phenoxy wherein the alkoxy group has from 1 to 8 carbons;

wherein p and q are integers from 0 to 20;

wherein n is 0 or 1; and wherein m is 0, 1, 2, or 3.

This invention also relates to a compound of the formula:

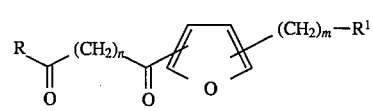

or a pharmaceutically acceptable salt thereof wherein X is oxygen, sulfur, —CH=CH—, or —CH=N—;

wherein $R^1$ is —$CO_2R^2$ or tetrazole;

wherein $R^2$ is hydrogen, alkyl of 1 to 6 carbons or a pharmaceutically acceptable cation;

wherein R is an alkyl of from 1 to 20 carbons, —$(CH_2)_pCF_3$ or —$(CH_2)_qR^3$ wherein $R^3$ is alkoxy, phenoxy or alkoxy substituted phenoxy wherein the alkoxy group has from 1 to 8 carbons;

wherein p and q are integers from 0 to 20;

wherein n is 0 or 1; and wherein m is 0, 1, 2, or 3.

DETAILED DESCRIPTION

This invention encompasses compounds of Formulae II–V as previously described. A particularly preferred embodiment of the present invention is encompassed by a compound of the formula:

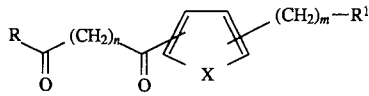

or a pharmaceutically acceptable salt thereof wherein X is oxygen, sulfur, —CH=CH—, or —CH=N—;

wherein $R^1$ is —$CO_2R^2$ or tetrazole;

$R^2$ is hydrogen, alkyl of 1 to 6 carbons or a pharmaceutically acceptable cation;

wherein R is an alkyl of from 1 to 20 carbons, —$(CH_2)_pCF_3$ or —$(CH_2)_qR^3$ wherein $R^3$ is alkoxy, phenoxy or alkoxy substituted phenoxy wherein the alkoxy group has from 1 to 8 carbons;

wherein p and q are integers from 0 to 20;

wherein n is 0 or 1; and wherein m is 0, 1, 2, or 3.

The term "lower alkyl" as used herein means straight or branched chain alkyls having 1–6 carbon atoms.

The term "pharmaceutically acceptable cation" as used to describe $R^2$ refers to cations such as ammonium, sodium, potassium, lithium, calcium, magnesium, ferrous, zinc, copper, manganous, aluminum, ferric, manganic, ammonium, tetraalkyl-ammonium, and the like.

The term "pharmaceutically acceptable salts" refers either to those non-toxic, base derived salts of any compound herein having a carboxylic acid function.

The base derived salts can be derived from pharmaceutically acceptable non-toxic inorganic or organic bases. Among the inorganic bases employed to produce pharmaceutically acceptable salts are the hydroxide bases of the "pharmaceutically acceptable cations" disclosed above.

Among the organic bases employed to produce pharmaceutically acceptable salts are the pharmaceutically acceptable non-toxic bases of primary, secondary, and tertiary amines. Especially preferred non-toxic bases are isopropylamine, diethylamine, ethanolamine, dicyclohexylamine, choline, and caffeine.

All of the pharmaceutically acceptable salts are prepared by conventional processes which are well known to those of ordinary skill in the art.

The compounds of this invention are generally prepared according to the reaction schemes I, II and III, wherein a side chain is substituted onto a halo aromatic acid or ester moiety. By halo is meant a halogen such as bromo, iodo or chloro. In Scheme I, the halo group is represented by the term "halo." By aromatic moiety is meant phenyl, pyridyl, thienyl or furyl, corresponding to "X" in the aryl ring being —CH=CH—, —CH=N—, —S—, and —O—.

As disclosed in the following reaction Schemes I–IV, an alkyne side chain can be added to an aromatic moiety by different techniques. The alkyne side chain is then hydrated with sulfuric acid, water and mercuric oxide to yield the indicated diketo product.

In Scheme I the alkyne side chain is added by performing a nucleophilic substitution of the halogen such as via a coupling reaction with an alkyne, CO, and Pd[O]. In Scheme II the alkyne side chain is added by acylation of a trimethylsilyl (TMS) acetylide with a diacid chloride in the presence of $AlCl_3$. In Scheme III the alkyne side chain is added via nucleophilic attack of an acetylide anion on an aldehyde with subsequent oxidation of the resulting alcohol. In Scheme IV the alkyne side chain is added via nucleophilic attack of an acetylide anion on an acid chloride.

The biological activity possessed by the compounds of this invention was indicated by positive results in assays for inhibition of human synovial fluid $PLA_2$ (HSF-$PLA_2$) and $LTB_4$ biosynthesis in HL-60 cells.

By virtue of their activity as $LTB_4$ synthesis inhibitors, the compounds of Formula I–VI are useful in treating inflammatory conditions in mammals such as psoriasis, Crohn's disease, ulcerative colitis, multiple sclerosis and the like. Similarly, the compounds of Formula I–VI can be used in preventing recurring inflammatory attacks. A physician or veterinarian of ordinary skill can readily determine whether a subject exhibits the inflammatory condition. The preferred utility relates to treatment of ulcerative colitis.

The compounds of the present invention can be administered in such oral dosage forms as tablets, capsules, soft gels, pills, powders, granules, elixirs, or syrups.

The compounds can also be administered intravascularly, intraperitoneally, subcutaneously, intramuscularly, or topically using forms known to the pharmaceutical art. Moreover, they can be administered rectally or vaginally, in such forms as suppositories or bougies. In general, the preferred form of administration is oral. For the orally administered pharmaceutical compositions and methods of the present invention, the foregoing active ingredients will typically be administered in admixture with suitable pharmaceutical diluents, excipients, or carriers (collectively referred to herein as "carrier" materials) suitably selected with respect to the intended form of administration, that is, oral tablets, capsules, soft gels, elixirs, syrups, drops, and the like, and consistent with conventional pharmaceutical practices.

For example, for oral administration in the form of tablets or capsules, a therapeutically effective amount of one or more compounds of the present invention can be combined with any oral non-toxic pharmaceutically acceptable inert carrier such as lactose, starch, sucrose, cellulose, magnesium stearate, dicalcium phosphate, calcium sulfate, mannitol, and the like, or various combinations thereof. For oral administration in liquid forms, such as in soft gels, elixirs, syrups, drops and the like, a therapeutically effective amount of the active drug components can be combined with any oral non-toxic pharmaceutically acceptable inert carrier such as water, saline, ethanol, polyethylene glycol, propylene glycol, corn oil, cottonseed oil, peanut oil, sesame oil, benzyl alcohol, various buffers, and the like, or various combinations thereof. Moreover, when desired or necessary, suitable binders, lubricants, disintegrating agents, and coloring agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes, or combinations thereof. Lubricants for use in these dosage forms include boric acid, sodium benzoate, sodium acetate, sodium chloride, and the like, or combinations thereof. Disintegrators include, without limitation, starch, methylcellulose, agar, bentonite, guar gum, and the like, or combinations thereof. Sweetening and flavoring agents and preservatives can also be included where appropriate.

For intravascular, intraperitoneal, subcutaneous, or intramuscular administration, one or more compounds of the present invention can be combined with a suitable carrier such as water, saline, aqueous dextrose, and the like. For topical administration, such as for psoriasis, therapeutically effective amounts of one or more compounds of the present invention can be combined with pharmaceutically acceptable creams, oils, waxes, gels and the like. Regardless of the route of administration selected, the compounds of the present invention are formulated into pharmaceutically acceptable dosage forms by conventional methods known to those skilled in the art. The compounds can also be formulated using pharmacologically acceptable base addition salts. Moreover, the compounds or their salts may be used in a suitable hydrated form.

Regardless of the route of administration selected, a non-toxic but therapeutically effective quantity of one or more compounds of this invention is employed in any treatment. The dosage regimen for preventing or treating inflammatory conditions with the compounds of this invention is selected in accordance with a variety of factors, including the type, age, weight, sex, and medical condition of the patient, the severity of the inflammatory condition, the route of administration, and the particular compound employed in the treatment. A physician or veterinarian of ordinary skill can readily determine and prescribe the effective amount of the drug required to prevent or arrest the progress of the condition. In so proceeding, the physician or veterinarian could employ relatively low doses at first and sequentially increase the dose until a maximum response is obtained. Daily dosages of the compounds of the invention are ordinarily in the range of about 1.0 mg/kg up to about 30.0 mg/kg, (preferably in the range of about 2.0 to 14.0 mg/kg (orally)).

The following examples illustrate the methods used to prepare the compounds of this invention. These examples are given by way of illustration only and are not meant to be construed as limiting the invention in spirit or in scope, as many modifications in materials and methods will be apparent from this disclosure to those skilled in the art.

In the structures herein a bond drawn across a bond in a ring indicates that the bond can be to any available carbon atom of the ring structure.

Scheme I

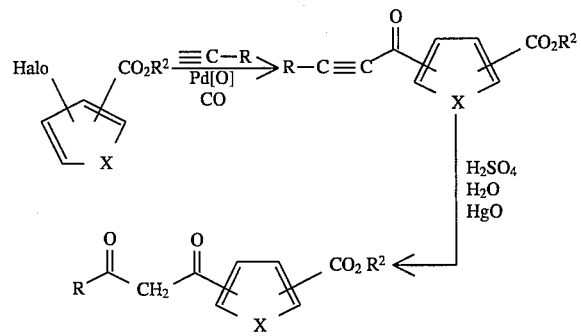

Scheme II

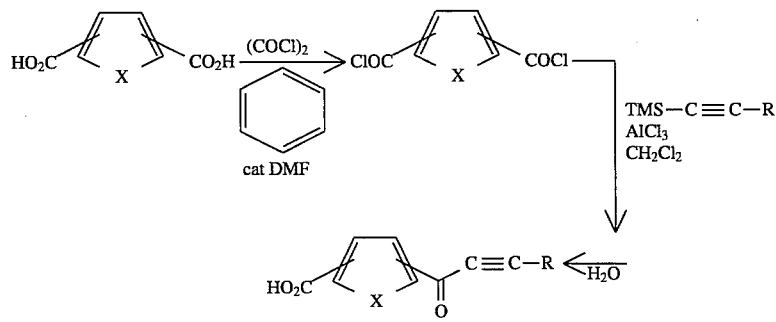

Scheme III

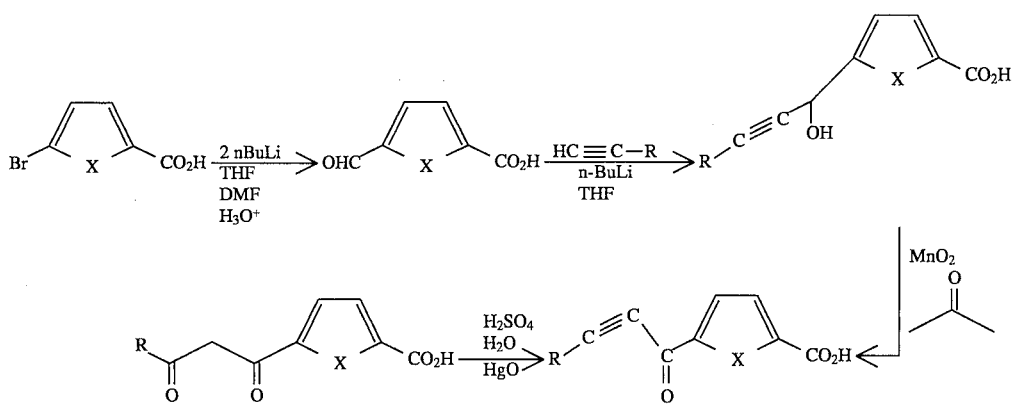

Scheme IV

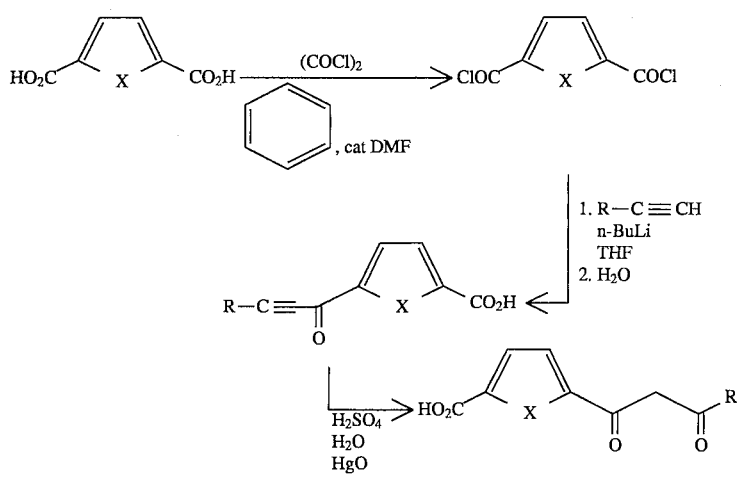

EXAMPLE 1

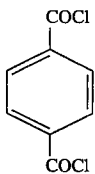

The above acid chloride was prepared from terphthalic acid by reacting 0.5 g (3 mmoles) of terphthalic acid with 2 cc of [COCl]$_2$ (23.6 mmoles) in 10 cc of benzene and with one drop of dimethylformamide. The reagents were mixed and warmed to 60° C. for twenty-four hours. The reaction mixture was cooled to room temperature and the volatile components were removed in vacuo to give the above compound as a pale yellow solid.

EXAMPLE 2

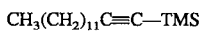

The above compound was prepared by reacting an acetylene of the formula CH$_3$(CH$_2$)$_{11}$C≡CH (2.5 g, 12.87 mmoles) which was added to 25 cc of tetrahydrofuran (THF) and 50 mg of triphenylmethane (Ph$_3$CH) which was added as an indicator. The solution was cooled to −30° C. and 1.6 molar n-butyllithium (n-BuLi) was added dropwise until the solution turned red. Approximately 8.5 cc of n-BuLi was added. The solution was back titrated with the acetylene compound until it became colorless. The solution was cooled to −78° C. and 2 cc (15.75 mmoles) of trimethylsilyl chloride (TMS—Cl) was added. The solution was slowly warmed over a period of five hours to room temperature. The reaction was quenched with water and extracted with hexane. The hexane was washed once with water and once with brine and dried over magnesium sulfate (MgSO$_4$). The trimethylsilyl compound was isolated in an amount of 4.31 g (16.2 mmoles).

EXAMPLE 3

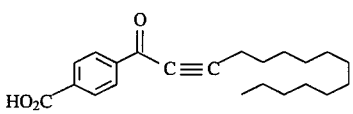

The above compound was prepared by reacting 3 mmoles of the acid chloride product from Example 1 with 0.8 g (3 mmoles) of the TMS-acetylene product from Example 2. The acid chloride and the TMS-acetylene product were dissolved in 10 cc of dichloromethane and cooled to 0° C. To the reaction mixture was added 0.8 g (6 mmoles) of aluminum chloride (AlCl$_3$) in small portions over ten minutes. The reaction mixture was stirred for about 1.5 hours at 0° C. The reaction was quenched with ice and the mixture was extracted three times with diethyl ether. The extracts were combined and washed once with water and once with brine (saturated NaCl solution) and dried over magnesium sulfate. Removal of the solvent in vacuo yielded 0.29 g of the above product. This was chromatographed on silica eluting with 15% ethyl acetate—85% hexane. HRMS (M$^+$): calculated 342.2195; found 342.2196

EXAMPLE 4

4-(1,3-dioxohexadecanyl)benzoic acid

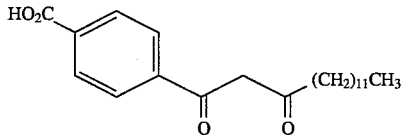

The product of Example 3, 27 mg was treated with 2 ml of cold H$_2$SO$_4$ which had been cooled in an ice bath. The mixture was stirred until all of the product had dissolved. To the reaction mixture was added 1 mg HgO. The reaction mixture was maintained cool in an ice bath. Two drops of water were added to the reaction mixture. The ice bath was removed and the reaction mixture was stirred and allowed to warm to room temperature for one half hour. The mixture was cooled to 0° C. and quenched with ice. The reaction mixture was diluted with water and extracted twice with ethyl acetate. The collected extracts were washed twice with water. The washed ethyl acetate fractions were collected and the volatile components removed and the residue chromatographed on silica gel (gradient elution) with 5% isopropyl alcohol, 95% Hexane +1% HOAc then 10% isopropyl alcohol, 90% Hexane +1% HOAc as eluant. 0.017 g of the above product was isolated.

Analysis: Calculated for 5H$_2$O: C, 71.51; H, 9.00 Found: C, 71.80; H, 8.72

EXAMPLE 5

3-(1,3-dioxohexadecanyl)benzoic acid

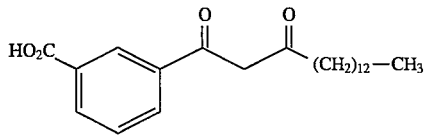

The above compound was prepared by mixing 9.42 g of m-iodobenzoic acid (38 mmoles) and 8 g (38.4 mmoles) of an acetylene derivative of the formula

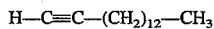

with 0.27 g (0.38 mmoles) of a palladium catalyst, pd(PPh$_3$)$_2$Cl$_2$ in 100 cc of diisopropyl amine. The reaction vessel was purged with carbon monoxide. The reaction mixture was heated under a carbon monoxide atmosphere (atmospheric pressure, balloon) in an oil bath at 80° C. for two hours. The reaction mixture was cooled to room temperature. The volatile components were removed in vacuo and the residue was taken up in 5% hydrochloric acid and extracted with diethyl ether. The diethyl ether was washed once with 10% hydrochloric acid, twice with water, and once with a brine solution and dried over magnesium sulfate. The solvent was removed yielding 18.65 gm of the product. A solid component was isolated from this mixture by chromatography on silica gel (10% isopropyl alcohol, 90% hexane, 1% HOAc). Recrystallization from CH$_2$Cl$_2$/Hexane afforded 0.66 g of the above product.

Analysis calculated: C, 73.76; H, 9.15 Found: C, 73.40; H, 9.13

EXAMPLE 6

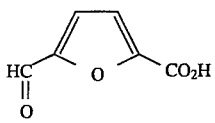

The above compound was prepared by forming a solution of 2.5 g (13.1 mmoles) of a bromo-furanoic acid in 25 ml of tetrahydrofuran (THF) which was cooled to −78° C. To the solution was added a 1.6 molar solution of n-butyl lithium in hexane (17.5 ml, 28 mmoles) which was stirred at −78° for one hour. Dimethylformamide (DMF) was added in an amount of 2.4 ml (30 mmoles). The solution was allowed to warm to room temperature. The reaction mixture was quenched with water and acidified with 10% hydrochloric acid. The resultant reaction mixture was extracted twice with ethyl acetate, the combined extracts were washed twice with water and once with brine and subsequently dried over magnesium sulfate. An orange solid was obtained after removal of the solvent in vacuo. Following chromatography on silica gel (gradient elution with EA-Hexane containing 1% HOAc) 0.73 gms. of the compound of the above formula was obtained.

EXAMPLE 7

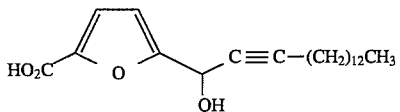

The above compound was prepared by forming a solution of 1.25 g (6 mmoles) of an acetylene of the formula H≡(CH$_2$)$_{12}$CH$_3$ in 25 ml. THF which contained 20 mg. of triphenylmethane which was added as an indicator. The solution was cooled to −50° C. and then treated with 3.75 ml. (6 mmoles) of n-BuLi until the red color of the triphenylmethane anion persisted. A few drops of the acetylene compound was added until the color disappeared. An amount of 0.42 gms. of the product formed in Example 6 in 10 ml. THF was added drop-wise to the solution. The mixture was warmed to 0° C. over one-half hour. The mixture was quenched with water and acidified with 10% hydrochloric acid. The aqueous phase was extracted twice with ethyl acetate. The extracts were combined and washed twice with water and once with brine and were dried over magnesium sulfate. Chromatography on silica gel (gradient elution with EA-Hexane containing 1% HOAc) yielded 0.80 gms. of a pale yellow solid.

HRMS (M⁺) Calculated: 348.2301; Found: 348.2291.

EXAMPLE 8

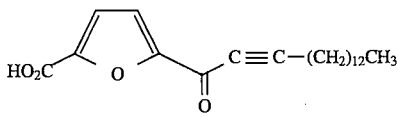

The compound was prepared by reacting 0.145 g. (4.2 mmoles) of the product from Example 7 in acetone (25 ml) and adding 1.5 g. of activated MnO₂ portionwise over five minutes. The reaction mixture was stirred for 24 hours at room temperature. The reaction mixture was poured into 10% hydrochloric acid and extracted with ethyl acetate. The extract was washed once with water and dried over magnesium sulfate. After the solvent was removed in vacuo a white solid remained. Following chromatography on silica gel (gradient elution with EA-Hexane containing 1% HOAc), 60 mg. of a white solid was recovered.

Analysis (for hydrate with 0.35 H₂O) Calculated: C, 71.50; H, 8.77 Found: C, 71.55; H, 8.63

EXAMPLE 9

5-(1,3-dioxohexadecanyl)-2-furancarboxylic acid

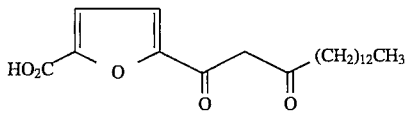

The product of Example 8, 22.5 mg was treated with 1 ml of cold H₂SO₄ which had been cooled in an ice bath. The mixture was stirred until all of the product had dissolved. To the reaction mixture was added 1 mg HgO. The reaction mixture was maintained cool in an ice bath. Two drops of water was added to the reaction mixture. The ice bath was removed and the reaction mixture was stirred and allowed to warm to room temperature for one half hour. The mixture was cooled to 0° and quenched with ice. The reaction mixture was diluted with water and extracted twice with ethyl acetate. The collected extracts were washed twice with water. The washed ethyl acetate fractions were collected and the volatile components removed and the residue chromatographed on silica gel (gradient elution) with 5% isopropyl alcohol, 95% Hexane +1% HOAc then 10% isopropyl alcohol, 90% Hexane +1% HOAc, which yielded 0.018 g of the above product.

Analysis: For 0.75 H₂O Calculated: C, 66.73; H, 8.93 Found: C, 66.69; H, 8.74

EXAMPLE 10

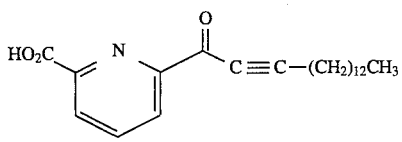

The above compound was prepared by forming a solution of 0.83 gms. (4 mmoles) of an acetylene of the formula H—C≡C—(CH₂)₁₂CH₃ in 25 ml. THF containing 20 mgs. of triphenyl methane as an indicator. The solution was cooled to −50° C., then treated with 2.5 ml. of a 1.6 molar solution (4 mmoles) of n-BuLi in hexane until the red color of the triphenylmethane anion persisted. A few drops of the acetylene was added until the color disappeared. The resultant lithium acetylide preparation was cooled to −78° C. A solution (6 mmoles) of a diacid chloride of the formula prepared from the corresponding diacid and oxalyl chloride in benzene (catalytic DMF) was cooled to −78° C. and the −78° C. solution of lithium acetylide was added dropwise via a cannula. The reaction was stirred for 10 minutes and quenched with water and warmed to room temperature. The reaction mixture was poured into water and acidified with acetic acid (HOAc). The aqueous solution was extracted twice with ethyl acetate and the extracts were washed twice with water, once with brine and dried over magnesium sulfate. Following chromatography on silica gel (gradient elution with isopropyl alcohol-hexane), 0.95 gms. of a product of the above formula was recovered.

Analysis calculated: C, 73.92; H, 8.74; N, 3.92 Found: C, 73.64; H, 8.79; N, 3.86

EXAMPLE 11

6-(1,3-dioxohexadecanyl)-2-pyridinecarboxylic acid

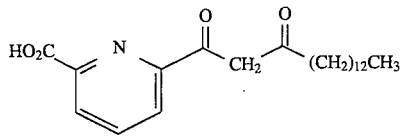

The product of Example 10, 25.6 mg was treated with 2 ml of cold H₂SO₄ which had been cooled in an ice bath. The mixture was stirred until all of the product had dissolved. To the reaction mixture was added 1 mg HgO. The reaction mixture was maintained cool in an ice bath. Two drops of water was added to the reaction mixture. The ice bath was removed and the reaction mixture was stirred and allowed to warm to room temperature for one half hour. The mixture was cooled to 0° and quenched with ice. The reaction mixture was diluted with water and extracted twice with ethyl acetate. The collected extracts were washed twice with water. The washed ethyl acetate fractions were collected and the volatile components removed and the residue chromatographed on silica gel (gradient elution) with 5% isopropyl alcohol, 95% Hexane +1% HOAc then 10% isopropyl alcohol, 90% Hexane +1% HOAc, which yielded 0.026 g of the above product.

Analysis: For 0.8H₂O Calculated: C, 67.77; H, 8.94; N, 3.59. Found: C, 67.71; H, 8.53; N, 3.43.

EXAMPLE 12

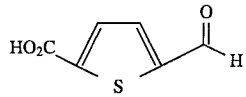

A compound of the above formula was prepared in the following manner. To a cooled (0° C.) solution of 5.5 ml. (39.2 mmoles) of diisopropylamine in 50 ml. of THF was added 20.5 ml. of 1.6 molar BuLi (32.8 mmoles) to make 32.8 mmoles of lithium diisopropylamide (LDA). The reaction mixture was stirred for one-half hour at 0° C and cooled to −78° C. To the mixture was added 2.1 g (16.4 mmoles) of 2-thiophene carboxylic acid in 25 ml. THF. Additional THF was added to increase the volume to 200 ml. and the reaction mixture was stirred for one-half hour. DMF was added in an amount of 1.3 ml. (16.8 mmoles). The reaction mixture was warmed to room temperature and stirred for 1½ hours. The reaction mixture was quenched with water and acidified with 1N hydrochloric acid and extracted with ethyl acetate. The organic extracts were combined and dried over magnesium sulfate. The resultant mixture was filtered and stripped to yield a yellow solid. Separation using chromatography on silica eluting with ethyl acetate/hexane/1% acetic acid provided 1.3 gms. of a yellow solid of the above formula. MP 160°–163°.

Analysis calculated: C, 46.15; H, 2.58 Found: C, 46.11; H, 2.82

EXAMPLE 13

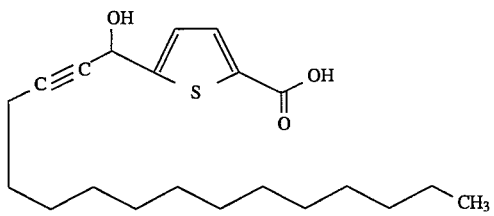

The compound with the above structure was prepared in the following manner. An acetylene of the formula H—C≡C—$(CH_2)_{12}CH_3$ in an amount of 549.3 mg. (2.6 mmoles) in 15 ml. of THF was cooled to −20°. To the solution was added 1.6 ml. (2.6 mmoles) of n-BuLi. The reaction was stirred for one half hour and 203.4 mg. (1.3 mmoles) of the product from Example 13 in 10 ml. of THF was added. The mixture was stirred and maintained at −20° for 15 minutes and allowed to warm to 0° C. and stirred for one-half hour. The reaction mixture was quenched with water and acidified with 10% hydrochloric acid and extracted with ethyl acetate. The combined organic extracts were dried over magnesium sulfate. The extract was filtered and stripped to yield a yellow oil which solidified upon standing. The solid was dissolved in ethyl acetate and filtered through silica gel eluting with 100% hexane followed by ethyl acetate in 1% acetic acid. The ethyl acetate fraction yielded 392.8 mg. of the above compound as a yellow solid having a melting point of 75°–90°.

Analysis calculated: C, 69.19; H, 8.85 Found: C, 69.18; H, 9.02

EXAMPLE 14

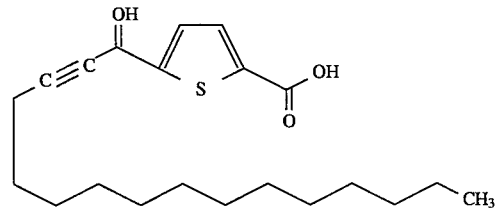

A compound of the above structure was formed in the following manner. 7.2 mg. (0.020 mmoles) of the compound prepared in Example 13 was dissolved in 1 ml. acetone. To the solution was added 72 mg. (0.83 mmoles) of activated manganese dioxide. The reaction mixture was stirred vigorously at room temperature overnight. The reaction mixture was poured into 10% hydrochloric acid. The aqueous phase was extracted with ethyl acetate. The organic washes were combined and dried over magnesium sulfate. The organic phase was filtered and stripped to yield 6 mg. (0.010 mmoles) of the above product as a white solid.

HRMS (M$^+$) Calculated: 362.1916 Found: 362.1910

EXAMPLE 15

5-(1,3-dioxohexadecyl)-2-thiophenecarboxylic acid

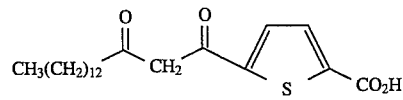

The compound of Example 14 (29.0 mg, 0.080 mmol) was dissolved in 2 ml of cold sulfuric acid. The reaction mixture was stirred until all of the solid dissolved. Two drops of water were added. After stirring for 10 minutes, the reaction mixture was placed in an oil bath at 60° C. for 1 hour. The mixture was cooled to 0° C. and quenched with ice. The aqueous phase was extracted three times with 20 ml ethyl acetate. The combined organic extracts were washed with saturated NaHCO$_3$ and dried over MgSO$_4$. The resultant oil was filtered through silica gel eluting with EA/1% acetic acid to yield 14.2 mg (0.037 mmol) of the above compound as a yellow solid.

HRMS (M$^+$) Calculated: 380.2022 Found: 380.1993

EXAMPLE 16

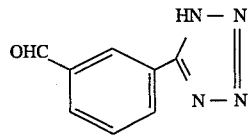

A compound having the above formula was prepared in the following manner. Two grams (15.2 mmoles) of m-cyano-benzaldehyde along with 2.98 gms. (45.8 mmoles) of NaN$_3$ and 2.9 gms. (21.1 mmoles) of Et$_3$N.HCl, were dissolved in 50 ml. of 1-methyl-2-pyrrolidinone. The reaction mixture was refluxed under argon. After 1 hour and 45 minutes the reaction mixture was cooled to room temperature and poured into 200 ml. of water and acidified with 10% hydrochloric acid. The reaction mixture was extracted with successive ethyl acetate washes. The ethyl acetate extracts were combined and washed with brine and dried over magnesium sulfate. The ethyl acetate extract was chromatographed through silica gel, yielding 0.3 gms. of the product having the above formula as a white solid.

EXAMPLE 17

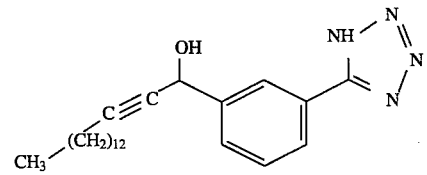

A compound of the above formula was prepared in the following manner. A solution of 542 mg (2.6 mmoles) of an acetylene of the formula HC≡C(CH$_2$)$_{12}$CH$_3$ was dissolved in 100 ml THF and cooled to −30° C. To the solution was added 1.6 ml. (2.6 mmoles) of a 1.6 molar n-BuLi solution which was added dropwise. The reaction mixture was stirred for 15 minutes at which time 219 mg. (1.26 mmoles) of the product from Example 16 dissolved in 8 ml. of THF was added dropwise. The solution was stirred and maintained at −30° C. for one-half hour, then warmed to room temperature. The reaction mixture was quenched with water and acidified with 10% hydrochloric acid. The layers were separated and the organic phase was washed with brine and dried over sodium sulfate. The layer was filtered and stripped to yield a yellow solid which upon chromatography over silica gel yielded 171.2 mg. of the above product as a white solid. M.P. 108°–110° C.

Analysis calculated: C, 72.21; H, 8.96; N, 14.65 Found: C, 72.03; H, 9.00; N, 14.77

EXAMPLE 18

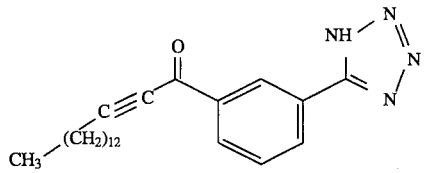

The compound having the above formula was prepared in the following manner. A solution was prepared by dissolving 36.2 mg (0.095 mmoles) of the product from Example 17 in acetone. To the solution was added 360 mg (4.14 mmoles) of activated manganese dioxide. The reaction mixture was stirred vigorously at room temperature overnight. The reaction mixture was poured into 10% hydrochloric acid. The aqueous phase was extracted with ethyl acetate and the organic washes were combined and dried over magnesium sulfate. The organic phase was filtered and stripped to yield 18 mg. of a pale yellow solid of a compound having the above formula.

Analysis calculated: C, 72.59; H, 8.48; N, 14.72 Found: C, 72.19; H, 8.66; N, 14.13

HRMS (M$^+$) Calculated: 380.2576 Found: 380.2579

EXAMPLE 19

1-[3-(1H-tetrazol-5-yl)phenyl]-1,3-hexadecadione

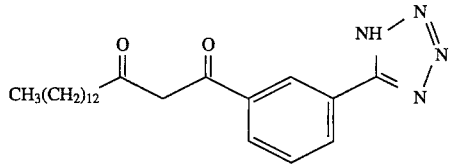

To 8 mg (0.021 mmol) of the compound produced in Example 18 was added 10 drops of cold H$_2$So$_4$. The reaction mixture was stirred for 5 minutes at which time about 1 mg of HgO was added. The reaction mixture was stirred at room temperature for 45 min. Water and ethyl acetate were added. The organic phase was washed with saturated NaHCO$_3$. The organic phase was collected and dried over MgSO$_4$. The organic phase was filtered and vacuum stripped to yield 7.6 mg of white solid.

HRMS (M$^+$) Calculated: 398.2682 Found: 398.2683

EXAMPLE 20

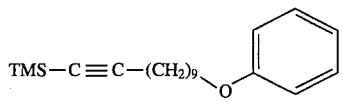

The above compound was prepared by reacting 2 g of phenol (21.2 mmol), 3.58 g of 10-undecyn-1-ol (21.2 mmol) and 5.57 g of triphenylphosphine (21.2 mmol) with stirring in 40 mls of tetrahydrofuran (THF) at room temperature under argon. A solution of 3.7 g diethyl azodicarboxylate (21.2 mmol) was added dropwise to the reaction mixture at room temperature. The solution was allowed to stand overnight. The reaction mixture was concentrated, dissolved in ether, filtered and concentrated. This yielded 3.5 g of the acetylene product having the following formula

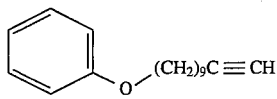

A 1 g portion of the above acetylene product (4.09 mmol) was dissolved in 25 ml of THF and 10 mg of triphenyl methane was added as an indicator. The solution was cooled to −30° C. and 2.6 ml of 1.6M n-butyl lithium (4.1 mmol) was added dropwise until the solution turned red. The solution was back-titrated with the acetylene product until colorless. The solution was cooled to −78° C. and 2 ml of trimethylsilyl chloride (15.8 mmol) was added. The solution was slowly warmed to room temperature. The reaction was quenched with water and extracted with hexane. The hexane extract was washed once with water and once with brine and dried over MgSO$_4$. The above product was recovered in an amount of 1.26 g.

EXAMPLE 21

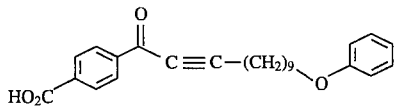

The above compound is prepared by reacting 3 mmoles of the acid chloride product from Example 1 with 0.95 g (3 mmoles) of the TMS-acetylene product from Example 20. The acid chloride and the TMS-acetylene product are dissolved in 10 cc of dichloromethane and cooled to 0° C. To the reaction mixture is added 0.8 g (6 mmoles) of aluminum chloride (AlCl$_3$) in small portions over ten minutes. The reaction mixture is stirred for about 1.5 hours at 0° C. The reaction is quenched with ice and the mixture is extracted three times with diethyl ether. The extracts are combined and washed once with water and once with brine (saturated NaCl) and dried over magnesium sulfate. Removal of the solvent in vacuo yields the above product.

EXAMPLE 22

4-(1,3-dioxo-12-phenoxydodecyl)benzoic acid

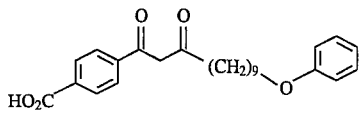

The product of Example 21, 27 mg is treated with 2 ml of cold H₂SO₄ which has been cooled in an ice bath. The mixture is stirred until all of the product has dissolved. To the reaction mixture is added 1 mg HgO. The reaction mixture is maintained cool in an ice bath. Two drops of water are added to the reaction mixture. The ice bath is removed and the reaction mixture is stirred and allowed to warm to room temperature for one half hour. The mixture is cooled to 0° C. and quenched with ice. The reaction mixture is diluted with water and extracted twice with ethyl acetate. The collected extracts are washed twice with water. The washed ethyl acetate fractions are collected and the volatile components removed and the residue chromatographed on silica which yields the above product.

EXAMPLE 23

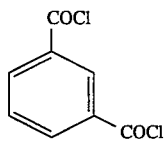

The above acid chloride was prepared from isophthalic acid by reacting 0.5 g (3 mmoles) of isophthalic acid with 2 cc of [COCl]₂ (23.6 mmoles) in 10 cc of benzene and with one drop of dimethylformamide. The reagents were mixed and warmed to 60° C. for twenty-four hours. The reaction mixture was cooled to room temperature and the volatile components were removed in vacuo to give the above compound.

EXAMPLE 24

CH₃O—(CH₂)₉—C≡C—TMS

The above product was prepared by placing 1 g of hydroxy acetylene (5.94 mmol) in 10 ml of THF and cooling to 0° C. To the solution was added 1 ml of methyl iodide which was followed by the portionwise addition of 0.4 g of sodium hydride (8.33 mmol). The reaction mixture was stirred and warmed to room temperature overnight. The reaction was quenched by pouring in to 100 ml of water, then extracted with hexane. The hexane was washed once with water and once with brine and dried over magnesium sulfate. Removal of the solvent in vacuo yielded 1.21 g of a pale yellow oil acetylene product of the following formula

CH₃O—(CH₂)₉—C≡CH

A 1 g portion of the above acetylene product (5.5 mmol) was dissolved in 25 ml of THF and 10 mg of triphenyl methane was added as an indicator. The solution was cooled to −30° C. and 3.4 ml of 1.6M n-butyl lithium (4.1 mmol) was added dropwise until the solution turned red. The solution was back-titrated with the acetylene product until colorless. The solution was cooled to −78° C. and 2 ml of trimethylsilyl chloride (15.8 mmol) was added. The solution was slowly warmed to room temperature. The reaction was quenched with water and extracted with hexane. The hexane extract was washed once with water and once with brine and dried over MgSO₄. The above product was recovered in an amount of 1.26 g.

EXAMPLE 25

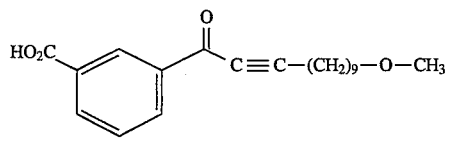

The above compound is prepared by reacting 3 mmoles of the acid chloride product from Example 23 with 0.76 g (3 mmoles) of the TMS-acetylene product from Example 24. The acid chloride and the TMS-acetylene product are dissolved in 10 cc of dichloromethane and cooled to 0° C. To the reaction mixture is added 0.8 g (6 mmoles) of aluminum chloride (AlCl₃) in small portions over ten minutes. The reaction mixture is stirred for about 1.5 hours at 0° C. The reaction is quenched with ice and the mixture is extracted three times with diethyl ether. The extracts are combined and washed once with water and once with brine (saturated sodium bicarbonate solution) and dried over magnesium sulfate. Removal of the solvent in vacuo yields 0.29 g of the above product.

EXAMPLE 26

3-(12-methoxy-1,3-dioxododecyl)benzoic acid

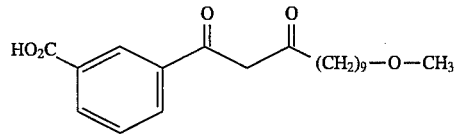

The product of Example 25, 27 mg is treated with 2 ml of cold H₂SO₄ which has been cooled in an ice bath. The mixture is stirred until all of the product has dissolved. To the reaction mixture is added 1 mg HgO. The reaction mixture is maintained cool in an ice bath. Two drops of water are added to the reaction mixture. The ice bath is removed and the reaction mixture is stirred and allowed to warm to room temperature for one half hour. The mixture is cooled to 0° C. and quenched with ice. The reaction mixture is diluted with water and extracted twice with ethyl acetate. The collected extracts are washed twice with water. The washed ethyl acetate fractions are collected and the volatile components removed and the residue chromatographed on silica gel which yields the above product.

EXAMPLE 27

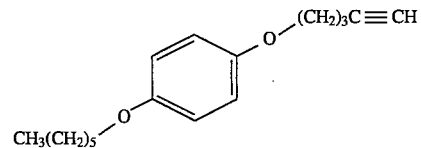

The above product is prepared by reacting 1.9 g (10 mmol) of p-hexoxyphenol, 2.1 g (20 mmol) 5-chloropentyne, 2.1 g potassium carbonate (15 mmol) in 50 ml of DMF, 100 mg of sodium iodide and heating to 40° C. for 16 hours. The reaction mixture is poured into water and extracted with hexane. The organic extract is washed once with 10% NaOH, once with water and once with brine and dried over magnesium sulfate. Removal of the solvent yields a gum. The gum is purified by column chromatography on silica to give the above acetylene product.

EXAMPLE 28

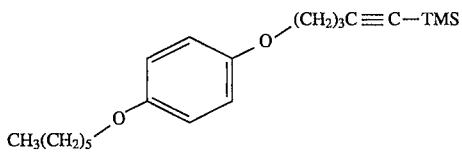

A 1 g portion of the acetylene product (3.8 mmol) of Example 27 is dissolved in 25 ml of THF and 10 mg of triphenyl methane is added as an indicator. The solution is cooled to −30° C. and 3.4 ml of 1.6M n-butyl lithium (4.1 mmol) is added dropwise until the solution turns red. The solution is back-titrated with the acetylene product until colorless. The solution is cooled to −78° C. and 2 ml of trimethylsilyl chloride (15.8 mmol) is added. The solution is slowly warmed to room temperature. The reaction is quenched with water and extracted with hexane. The hexane extract is washed once with water and once with brine and dried over MgSO$_4$. After removal of the solvent the above product is recovered.

EXAMPLE 29

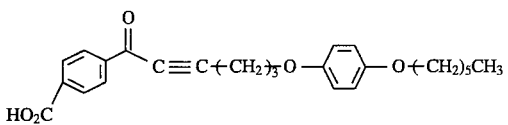

The above compound is prepared by reacting 3 mmoles of the acid chloride product from Example 1 with 1.0 g (3 mmoles) of the TMS-acetylene product from Example 28. The acid chloride and the TMS-acetylene product are dissolved in 10 cc of dichloromethane and cooled to 0° C. To the reaction mixture is added 0.8 g (6 mmoles) of aluminum chloride (AlCl$_3$) in small portions over ten minutes. The reaction mixture is stirred for about 1.5 hours at 0° C. The reaction is quenched with ice and the mixture is extracted three times with diethyl ether. The extracts are combined and washed once with water and once with brine (saturated NaCl) and dried over magnesium sulfate. Removal of the solvent in vacuo yields the above product.

EXAMPLE 30

4-[6-[4-(hexyloxy)phenoxy]-1,3-dioxohexyl]benzoic acid

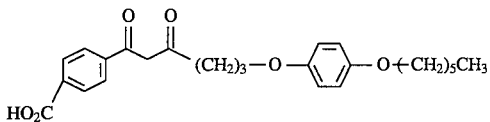

The product of Example 29, 27 mg is treated with 2 ml of cold H$_2$SO$_4$ which has been cooled in an ice bath. The mixture is stirred until all of the product has dissolved. To the reaction mixture is added 1 mg HgO. The reaction mixture is maintained cool in an ice bath. Two drops of water are added to the reaction mixture. The ice bath is removed and the reaction mixture is stirred and allowed to warm to room temperature for one half hour. The mixture is cooled to 0° C. and quenched with ice. The reaction mixture is diluted with water and extracted twice with ethyl acetate. The collected extracts are washed twice with water. The washed ethyl acetate fractions are collected and the volatile components removed and the residue chromatographed on silica which yields the above product.

EXAMPLE 31

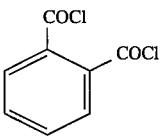

The above acid chloride was prepared from phthalic acid by reacting 0.5 g (3 mmoles) of phthalic acid with 2 cc of [COCl]$_2$ (23.6 mmoles) in 10 cc of benzene and with one drop of dimethylformamide. The reagents were mixed and warmed to 60° C. for twenty-four hours. The reaction mixture was cooled to room temperature and the volatile components were removed in vacuo to give the above compound.

EXAMPLE 32

TMS—C≡C—(CH$_2$)$_4$CF$_3$

The above compound is prepared by first preparing a 1-trifluoro-5-bromopentane by the reaction of 5-bromopentanoic acid with SF$_4$. The reaction is conducted by mixing 50.166 g (0.2771 mmol) of the 5-bromopentanoic acid with 120 g (1.111 mmol) of SF$_4$ and heating in a pressure vessel. A 12.5 g (0.3 mmol) amount of NaF was added in 50 ml methylene chloride. The reaction mixture was filtered and washed with about 60 ml of methylene chloride. The methylene chloride was washed once with water and once with NaHCO$_3$ and once with brine and dried over magnesium sulfate. Removal of the solvent in vacuo gave a brown oil which was distilled and the 25°–30° C. fraction collected yielding 42.73 g of 1-trifluoro-5-bromopentane. Trimethylsilyl-acetylene, 5 g (50.9 mmol) was mixed with 50 mg of triphenylmethane in 200 ml of THF and cooled to −50° C. and 1.6M n-butyl lithium in hexane was added dropwise (about 33 ml) until a red color persisted. A small portion of trimethylsilyl acetylene was added until the red color disappeared. The mixture was warmed to −20° C. and stirred for one half hour. The reaction mixture was cooled to −40° C. and 10 g of the trifluoro-5-bromopentane was added dropwise. Then 50 ml of HMPA was added dropwise and the reaction mixture was stirred and warmed to room temperature. The reaction was quenched with water and was poured into one liter of hexane. The mixture was washed four times with water, once with brine and dried over magnesium sulfate. The solvent was stripped in vacuo to give a brown liquid that was distilled. The fraction boiling between 65°–68° C. was collected and gave 5.0 g of the above TMS acetylene product.

EXAMPLE 33

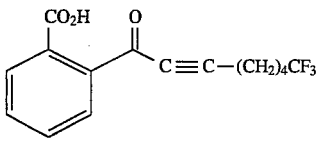

The above compound is prepared by reacting 3 mmoles of the acid chloride product from Example 31 with 0.66 g (3 mmoles) of the TMS-acetylene product from Example 32. The acid chloride and the TMS-acetylene product are dissolved in 10 cc of dichloromethane and cooled to 0° C. To the reaction mixture is added 0.8 g (6 mmoles) of aluminum chloride ($AlCl_3$) in small portions over ten minutes. The reaction mixture is stirred for about 1.5 hours at 0° C. The reaction is quenched with ice and the mixture is extracted three times with diethyl ether. The extracts are combined and washed once with water and once with brine (saturated NaCl) and dried over magnesium sulfate. Removal of the solvent in vacuo yields the above product.

EXAMPLE 34

2-(8,8,8-trifluoro-1,3-dioxooctyl)benzoic acid

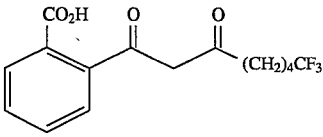

The product of Example 33, 27 mg is treated with 2 ml of cold $H_2SO_4$ which has been cooled in an ice bath. The mixture is stirred until all of the product has dissolved. To the reaction mixture is added 1 mg HgO. The reaction mixture is maintained cool in an ice bath. Two drops of water are added to the reaction mixture. The ice bath is removed and the reaction mixture is stirred and allowed to warm to room temperature for one half hour. The mixture is cooled to 0° C. and quenched with ice. The reaction mixture is diluted with water and extracted twice with ethyl acetate. The collected extracts are washed twice with water. The washed ethyl acetate fractions are collected and the volatile components removed and the residue chromatographed on silica which yields the above product.

EXAMPLE 35

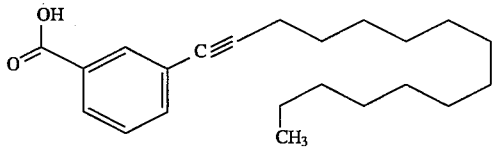

To a reaction vessel was added m-iodobenzoic acid (1 g, 4.03 mmoles) 0.83 g acetylene (4.0 mmoles) of the formula H—C≡C—$C_{13}H_{27}$, 46 mg of a palladium catalyst Pd (PPh$_3$)$_4$ (0.04 mmoles) in 10 ml of diethylamine. The reaction vessel was degassed with argon. To the reaction vessel was added 0.15 g of copper iodide (0.8 mmoles). The reaction mixture was stirred under argon for 2½ days. The volatile components were removed in vacuo and the residue was treated with 10% hydrochloric acid. The aqueous solution was extracted with ethyl acetate and the extract was washed with 10% hydrochloric acid, water and brine. The extract was dried over magnesium sulfate. The solvent was removed in vacuo to give a brown gummy solid. This residue was chromatographed on silica eluting with 10% ethyl acetate-90% hexane-1% acetic acid to yield 1.19 g (3.6 mmoles) of a white solid of the above identified compound.

Analysis Calculated: C, 80.44; H, 9.82 Found: C, 80.65; H, 10.08

EXAMPLE 36

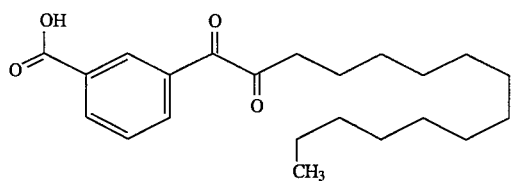

The compound of Example 35, 0.33 g (1 mmole) was taken up in a solvent mixture consisting of 4.6 ml of $CCl_4$, 4.6 ml of $CH_3CN$ and 7 ml of water followed by addition of $NaIO_4$ (0.88 g, 4.1 mmoles) which was added in one portion. The reaction mixture was stirred for 10 minutes until a clear solution (two phase) formed. To the solution was added 0.0029 g (0.022 mmoles) of $RuO_2$. The reaction mixture was stirred for about 18 hours at room temperature. The reaction mixture was transferred to a separatory funnel and the organic layer separated. The aqueous layer was extracted with dichloromethane. The combined extracts were dried over magnesium sulfate and filtered through celite. Evaporation of the solvent followed by chromatography on silica eluting with 2:1 hexane-diethylether (1% HOAc) yielded 0.12 g of the above identified compound.

Calculated: C, 73.30; H, 8.95 Found: C, 73.11; H, 8.94

EXAMPLE 37

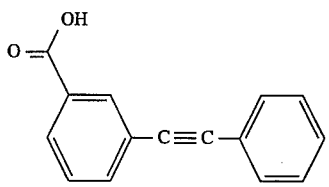

To a reaction vessel was added 3 g of m-iodobenzoic acid (12.1 mmoles) and 1.53 g of acetylene (15 mmoles) of the formula Ph—C≡C—H. To the reaction vessel was added a palladium catalyst 0.085 g (0.121 mmoles of Pd(PPh$_3$)$_2$Cl$_2$ in 30 ml of diethylamine. The reaction mixture was heated in an oil bath to 90° C. for 2 hours. The reaction mixture was cooled to room temperature. The volatile components were removed in vacuo leaving a residue of a dark red solid. The residue was crystallized from diethyl ether and hexane and triturated with hexane to give 1.64 g of a yellow solid of the above structure.

Analysis Calculated: Calculated for 0.1H$_2$O: C, 80.41; H, 4.59 Found: C, 80.49; H, 4.77

EXAMPLE 38

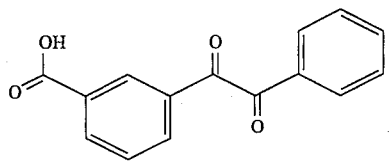

The product of Example 37, 0.22 g (1 mmole) was taken up in a solvent consisting of 4.6 ml of $CCl_4$, 4.6 ml of $CH_3CN$ and 7 ml of water to which was added $NaIO_4$ (0.88 g, 4.1 mmoles). The reaction mixture was stirred for 10 minutes until a clear solution (two phase) developed. To the reaction mixture was added 0.0029 g (0.022 mmoles) of $RuO_2$. The reaction mixture was stirred for approximately 18 hours at room temperature. The mixture was transferred to a separatory funnel and the organic layer was separated. The aqueous layer was extracted with dichloromethane. The combined extracts were dried over $MgSO_4$ and filtered through celite. Evaporation of the solvent followed by chromatography on silica eluting with 2:1 hexane/diethyl ether (1% HOAc) yielded 0.156 g of the above identified compound.

Analysis Calculated for $0.1H_2O$: C, 70.37; H, 4.02 Found: C,70.23; H,4.07

ASSAY FOR $LTB_4$ AND $PGE_2$ PRODUCTION BY HL-60 CELLS

HL-60 cells were induced to differentiate into granulocytes by a 4 day incubation with 0.8% (v/v) N,N-dimethyl formamide as disclosed in Fontana et al., Proc. Natl. Acad. Sci. 78 (6):3863–3866 (1981); Agins et al., Biochem. Biophys. Res. Comm. 126, 143–149 (1985); and Bonser et al., Biochemistry 20: 5297–5301 (1981). Prior to performing the assay, differentiated HL-60 cells were washed once with Hanks' balanced salt solution containing 0.35 mg/ml sodium bicarbonate and 10 mM HEPES pH 7.35 (HBSS). HL-60 cells ($3\times10^6$ cells/ml) were pre-incubated with the compound tested or a control vehicle at 37° C. for 10 minutes, followed by 5 minute incubation with $5\times10^{-6}M$ calcium ionophore A23187 in a final volume of 1.0 ml. After incubation, the cells were pelleted by centrifugation and the $LTB_4$ and $PGE_2$ in the supernatent were quantified by radioimmunoassay. $IC_{50}$ values (means ±S.E.) for compounds herein that were tested are shown in the following Table and represent the concentrations of the compound required to inhibit 50% of $LTB_4$ or $PGE_2$ production by HL-60 cells stimulated with the calcium ionophore A23187.

HUMAN SYNOVIAL FLUID PHOSPHOLIPASE $A_2$ (HSF-PLA$_2$) ASSAY

Human synovial fluid phospholipase $A_2$ was purified approximately 5000 fold following the procedures of Franson et al., Lung 160, 275–284 (1982) and Fawzy et al., Bio Phys. J. 49, 533a (1986). Following purification the enzyme activity was measured by established methodology using [$^{14}$C]-oleate-labeled, autoclaved E. coli as the substrate as also shown in the above noted references. The assay was performed in a final volume of 100 µl containing 50 mM HEPES (pH 7.0), 150 mM NaCl, 5 mM $CaCl_2$, 7 nM [$^{14}$C]-oleate-labeled E. coli phospholipid and with or without the compound from one of the examples herein undergoing an assay. The compound or control vehicle was pre-incubated with the $PLA_2$ for 5 minutes followed by addition of the E. coli substrate to initiate the reaction. The reaction was maintained at 37° C. for 30 minutes and then terminated by the addition of 2 ml tetrahydrofuran (THF). The reaction product, [$^{14}$C]-oleic acid, was extracted using a 1 ml Bond Elut-$NH_2$ Solid phase extraction column. The $IC_{50}$ value for the compound (mean ±S.E.) is given in the following Table and represents the concentration of the compound required to inhibit 50% of the $PLA_2$ activity.

TABLE

| Example # | HSF-PLA2 IC50 µM | LTB4 Biosynthesis inhibition cells IC50 µM | |
|---|---|---|---|
| | | Human PMNs | HL60 cells |
| 5 | 1.7 | 1.2 | 1.5 |
| 4 | 90 | | |
| 9 | 2.7 | 3.5 | 4.7 |
| 19 | 48 | 3.0 | |
| 15 | 1.9 | 2.7 | |
| 22 | 16 | 2.7 | |

We claim:

1. A pharmaceutical composition comprising a compound of the formula

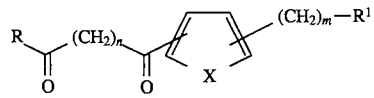

or a pharmaceutically acceptable salt thereof
  wherein X is —CH=CH—;
  wherein $R^1$ is —$CO_2R^2$;
  wherein $R^2$ is hydrogen, alkyl of 1 to 6 carbons or a pharmaceutically acceptable cation;
  wherein R is an alkyl of from 1 to 20 carbons, —$(CH_2)_pCF_3$ or —$(CH_2)_qR^3$ wherein $R^3$ is alkoxy, phenoxy or alkoxy substituted phenoxy wherein the alkoxy group has from 1 to 8 carbons;
  wherein p and q are integers from 0 to 20;
  wherein n is 1; and
  wherein m is 0, 1, 2, or 3;
  and a pharmaceutically acceptable carrier.

2. A method for the treatment of mammals exhibiting an $LTB_4$ mediated inflammatory condition, comprising administering a compound of the formula

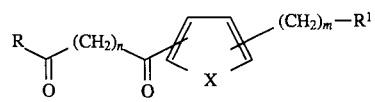

or a pharmaceutically acceptable salt thereof
  wherein X is —CH=CH—;
  wherein $R^1$ is —$CO_2R^2$;
  wherein $R^2$ is hydrogen, alkyl of 1 to 6 carbons or a pharmaceutically acceptable cation;
  wherein R is an alkyl of from 1 to 20 carbons, —$(CH_2)_pCF_3$ or —$(CH_2)_qR^3$ wherein $R^3$ is alkoxy, phenoxy or alkoxy substituted phenoxy wherein the alkoxy group has from 1 to 8 carbons;
  wherein p and q are integers from 0 to 20;
  wherein n is 1; and
  wherein m is 0, 1, 2, or 3.

3. A pharmaceutical composition according to claim 1 wherein m is zero.

4. A pharmaceutical composition according to claim 1 wherein $R^1$ is —$CO_2H$.

5. A pharmaceutical composition according to claim 1 wherein R comprises an alkyl group of 10 to 15 carbons.

6. A pharmaceutical composition according to claim 5 wherein the compound is 3-(1,3-dioxohexadecanyl)benzoic acid.

7. A pharmaceutical composition according to claim 5 wherein the compound is 4-(1,3-dioxohexadecanyl)benzoic acid.

8. A method according to claim 2 wherein m is zero.

9. A method according to claim 2 wherein $R^1$ is —$CO_2H$.

10. A method according to claim 2 wherein R comprises an alkyl group of 10 to 15 carbons.

11. A method according to claim 10 wherein the compound is 3-(1,3-dioxohexadecanyl)benzoic acid.

12. A method according to claim 10 wherein wherein the compound is 4-(1,3-dioxohexadecanyl)benzoic acid.

\* \* \* \* \*